(12) United States Patent
Cole

(10) Patent No.: US 6,525,239 B2
(45) Date of Patent: Feb. 25, 2003

(54) THONG PANTILINER WITH IMPROVED WICKING CHARACTERISTICS

(75) Inventor: Robert T. Cole, Jackson, NJ (US)

(73) Assignee: Tyco Healthcare Retail Services AG (CH)

( * ) Notice: Subject to any disclaimer, the term of this patent is extended or adjusted under 35 U.S.C. 154(b) by 0 days.

(21) Appl. No.: 09/788,931

(22) Filed: Feb. 20, 2001

(65) Prior Publication Data
US 2002/0115978 A1 Aug. 22, 2002

(51) Int. Cl.[7] .................................................. A61F 13/15
(52) U.S. Cl. .................................. 604/382; 604/385.101
(58) Field of Search ................................ 604/379, 380, 604/385.101, 385.01, 381, 382

(56) References Cited

U.S. PATENT DOCUMENTS

| | | | |
|---|---|---|---|
| 3,805,790 A | | 4/1974 | Kaczmarzyk et al. |
| 4,079,739 A | * | 3/1978 | Whitehead .................. 604/365 |
| D272,189 S | | 1/1984 | Sneider |
| D272,190 S | | 1/1984 | Sneider |
| D276,184 S | | 10/1984 | Whitehead |
| 4,624,666 A | | 11/1986 | DeRossett et al. |
| 4,758,240 A | | 7/1988 | Glassman |
| 5,104,396 A | | 4/1992 | Oatley et al. |
| 5,447,506 A | | 9/1995 | Lindquist |
| 5,451,442 A | | 9/1995 | Pieniak et al. |
| D366,524 S | | 1/1996 | Chung |
| D368,519 S | | 4/1996 | Harrison et al. |
| 5,613,960 A | | 3/1997 | Mizutani |
| 5,683,373 A | | 11/1997 | Darby |
| D392,736 S | | 3/1998 | Erickson |
| 5,729,835 A | | 3/1998 | Williams |
| D394,503 S | | 5/1998 | Perrini |
| 5,795,344 A | | 8/1998 | Chappell |
| 5,807,365 A | * | 9/1998 | Luceri ........................ 604/358 |
| 5,891,118 A | | 4/1999 | Toyoshima et al. |
| D411,006 S | | 6/1999 | Nixon et al. |
| D416,324 S | | 11/1999 | Nixon et al. |
| D424,195 S | | 5/2000 | Talon |
| D425,196 S | | 5/2000 | Nixon et al. |
| D431,293 S | | 9/2000 | Finkle et al. |

* cited by examiner

Primary Examiner—Dennis Ruhl
Assistant Examiner—Jamisue A. Webb
(74) Attorney, Agent, or Firm—Caesar, Rivise, Bernstein, Cohen & Pokotilow, Ltd.

(57) ABSTRACT

A disposable absorbent thong-shaped pantiliner. The pantiliner is in the form of a generally planar pad having a longitudinal central axis and a generally wedge-shaped periphery including first and second generally concave longitudinal extending sides interconnecting a top end and a bottom end. The pad includes a fluid-pervious top sheet an absorbent core and a fluid impervious back sheet that are bonded together along a first set of non-linear, parallel lines and second set of linear parallel lines. The first set of lines have portions extending generally along each side and the top and bottom end of the pad. The first set of lines also has a fourth portion extending generally along the bottom end of the pad. The second set of lines are located adjacent the bottom end of the pad and extend parallel to the longitudinal axis. The first set of parallel lines merge with the second set of parallel lines adjacent the bottom end of the pad. The parallel lines forming a barrier resistant to the egress of fluid out of the periphery of said pad and serve to channel fluid therealong to spread the fluid across the pad.

21 Claims, 2 Drawing Sheets

THONG PANTILINER WITH IMPROVED WICKING CHARACTERISTICS

FIELD OF THE INVENTION

This invention relates generally to disposable absorbent articles and more specifically to disposable absorbent articles, e.g., thong pantiliners, that are comfortable and exhibit enhanced resistance to peripheral or side leakage.

BACKGROUND OF THE INVENTION

Disposable absorbent sanitary articles, e.g., such as pantiliner pads, frequently make use of one or more lines or grooves to deter the egress of liquid out of the article. For example, U.S. Pat. No. 5,807,365 (Luceri) discloses a disposable shield of a generally dog-bone shape comprising a thin, highly absorbent pad having a body-contacting surface, an absorbent layer, a liquid barrier, a positioning adhesive for attaching the pad to an undergarment, and a release layer to protect the adhesive prior to use. The pad further comprises densified areas forming unbroken concentric rings having the same general shape as the shield itself. These rings are made by fusing all pad layers together in a pattern embosser to create densified areas resistant to the flow of liquid therethrough. The densified areas are made contiguous such that fluid, when introduced or deposited on the pad, will be prevented or hindered from flowing to the edges of the pad. Moreover, the concentric rings serve to separate, or compartmentalize, the pad into distinct absorbing areas which are isolated from each other.

U.S. Pat. No. 5,795,344 (Chappell) discloses an absorbent article, such as a sanitary napkin having a cover, a baffle and an absorbent between the cover and baffle and includes a single, unbroken embossed channel positioned inward from the peripheral edge of the article. The channel impedes the flow of fluid toward the edges of the absorbent article and increases absorbent utilization in the absorbent article. The channel can be produced various ways, such as by application of heat, including hot calendar embossing or by using ultrasonic means.

U.S. Pat. No. 5,891,118 (Toyoshima et al) discloses elongated absorbent articles that includes an antileakage groove formed along each longitudinal side portion of the article. The antileakage groove may be continuous or discontinuous and only extends partially into the thickness of the article.

Other United States Letters Patents disclosing absorbent articles or pads with channels, grooves or embossed or debossed lines are: U.S. Pat. No. 4,624,666 (DeRossett et al), U.S. Pat. No. 4,758,240 (Glassman), U.S. Pat. No. 5,104,396 (Oatleyetal), U.S. Pat. No. 5,447,506 (Lindquist), U.S. Pat. No. 5,451,442 (Pieniak et al) and U.S. Pat. No. 5,613,960 (Mizutani). Various United States Design Patents also disclose absorbent articles or pads with channels, grooves or embossed or debossed lines, such as U.S. Design Pat. No. 272,189 (Sneider) and U.S. Design Pat. No. 272,190 (Sneider), Pantiliners or other sanitary disposable absorbent articles or pads are also commercially available that make use of at least one barrier line to prevent the egress of liquid from a peripheral portion of the article. For example, a "regular maxipad" sold under the trademark FRESH TIMES® by The Kendall Confab Retail Group, a division of the assignee of this invention, basically comprises an hour-glass shaped pad having an outer sheet or cover formed of a fluid-impervious, e.g., plastic, material, an inner liner formed of a fluid-pervious, e.g., non-woven, material, and an absorbent core, e.g., fluff and/or SAP, etc., interposed therebetween. In order to prevent leakage of the liquid which is absorbed through the inner liner into the core, the FRESH TIMES® pad is embossed, e.g., heat sealed, along a broken line generally conforming to the periphery of the pad. The breaks or gaps in the line are provided in the interest of maintaining flexibility of the pad so that it can conform to the crotch area of the wearer. To that end, the embossed line is broken at two points along both of the long sides of the pad spaced from the center of those sides and just at the interface with the ends of the line. The unbroken portions of the embossed line serve as a barrier to prevent the migration of liquid through it and out of either marginal side edge of the pad or out of either marginal end edge of the pad.

While all of the foregoing absorbent articles are suitable for their intended purposes, they never the less leave something to be desired from the standpoint of retention of fluid, (e.g., resistance to leakage) flexibility and conformability to the body of the wearer.

In U.S. patent application, Ser. No. 09/624,088 filed on Jul. 24, 2000, entitled Light Incontinent Product, which is assigned to the same assignee as this invention, and whose invention is incorporated by reference herein, there is disclosed and claimed a pantiliner or other absorbent pad, arranged to be worn by a wearer to trap and collect fluid waste products of the wearer and a method of making the absorbent article. The pad is an elongated generally planar member having a periphery, e.g., a general hour-glass shape, including a pair of longitudinal extending, e.g., concave, sides interconnecting respective ones of a pair of ends, e.g., convex ends. The pad basically comprising a top-sheet, a fluid absorbent core, and a cover sheet. The top sheet is formed of a fluid pervious material, e.g., a non-woven material, and is disposed over the absorbent core. The absorbent core comprises a fluid absorbing material, e.g., cellulosic fluff and super-absorbent particles, and is disposed over the cover sheet. The cover sheet is formed of a fluid impervious material, e.g., a plastic film. The top-sheet, the fluid absorbent core and the cover sheet are bonded together along plural concentric lines located adjacent the sides and plural concentric lines adjacent the ends, e.g., plural concentric lines which are themselves concentric with the periphery of the pad. The plural concentric lines form a barrier resistant to the egress of fluid out of the periphery of the pad and include at least one gap therein to facilitate the bending of the pad.

While the invention of the aforementioned patent application is generally suitable for its intended purposes it never the less leaves something to be desired from the standpoint of suitability for use under a thong.

The prior art does include various pantiliners for use with thong shaped garments. For example, U.S. Design Pat. No. 366,524 (Chung) discloses a thong pantiliner that has one bulbous end that tapers down to a narrower, slightly arced end. The width of the bulbous end is approximately two and one half times that of the narrow end. The bottom view has a pattern of four undulating lines on its surface.

U.S. Design Pat. No. 424,195 (Talon) discloses a thong pantiliner that is generally heart shaped with a top having two lobes separated by a distinct point and two substantially straight sides angling down to an end. The end has a rounded point having a radius less than half of the radius of the lobes. The top view has a "quilting" pattern of diamonds with flowers at the corners of the diamonds.

U.S. Design Pat. No. 392,736 (Erickson) discloses a pantiliner somewhat similar in overall shape (in the top view) to that of U.S. Design Pat. No. 366,524 (Chung). Here, however, the corners are somewhat sharper and the bottom is not arced, but is straight. The top view has a pattern of undulating lines (different than that of the Chung patent). The side views (FIGS. 4 and 5) indicate a two-step surface where a bottom layer is longer than a top layer.

U.S. Design Pat. No. 431,293 (Finkle et al.) discloses a feminine hygiene sanitary pad that is thong shaped with an overall shape (in the top view) similar to that of U.S. Des. Pat. No. 366,524 (Chung) and U.S. Des. Pat. No. 392,736 (Erickson). Here, however, the top surface slopes downwardly adjacent the edges as can be seen in FIGS. 1 and 2–5.

U.S. Pat. No. 5,683,373 (Darby) discloses a sanitary napkin shaped for use with a thong garment. The pad is v-shaped in plan view, bulbous at first top end having a predetermined width, and tapering therefrom longitudinally to a midportion, and from there longitudinally narrowing in an elongated lower end portion terminating in a second end. The lower end portion has a substantially uniform width, less than twenty-five percent of the width of the bulbous first end portion and a length greater than one third, but less than one half the total length of the pad from longitudinal end to end.

U.S. Pat. No. 5,729,835 (Williams) is directed to a pantiliner for use with thong shaped underwear having an upper first layer fabricated of a cotton panel, a second layer fabricated of a cotton weave, a third layer fabricated of an absorbent material, a fourth layer fabricated of a cotton weave, a fifth layer fabricated of a plastic material, a sixth layer fabricated of a cotton panel, an adhesive strip, and a protective backing for the adhesive strip.

Other thong shaped pantiliners are disclosed in the following United States design patents: U.S. Des. Pat. No. 276,184 (Whitehead), U.S. Des. Pat. No. 368,519 (Harrison et al.), U.S. Des. Pat. No. 394,503 (Perrini), U.S. Des. Pat. No. 411,006 (Nixon et al.), U.S. Des. Pat. No. 416,324 (Nixon et al.), U.S. Des. Pat. No. 425,196 (Nixon et al.), and U.S. Pat. No. 3,805,790 (Kaczmarzyk et al.).

While the aforementioned thong shaped pantiliners are generally suitable for their intended purposes they never the less leave something to be desired from the standpoint resistance to peripheral or side leakage.

SUMMARY OF THE INVENTION

This invention relates to a disposable absorbent article in the form of pantiliner for use under a thong garment to trap and collect fluid waste products of the wearer and a method of making the absorbent article. The pad is an elongated generally planar member having a generally wedge-shaped periphery, e.g., of a tear-drop shape, etc., including a pair of generally longitudinal extending, e.g., concave, sides interconnecting a top end, e.g., a convex or somewhat concave edge, and a bottom end, e.g., a convex edge. The top end has a substantially longer periphery than the bottom end, The pad basically comprising a top-sheet, a fluid absorbent core, and a cover or back sheet. The top sheet is formed of a fluid pervious material, e.g., a non-woven material, and is disposed over the absorbent core. The absorbent core comprises a fluid absorbing material, e.g., cellulosic fluff and super-absorbent particles, and is disposed over the cover or back sheet. The cover or back sheet is formed of a fluid impervious material, e.g., a plastic film.

The top sheet, fluid-absorbent core and the back sheet are bonded together along first and second sets of plural generally parallel lines. The first set of lines are non-linear while the second set lines are linear. The first set of lines have respective first portions extending generally along the first side of said pad, respective second portions extending generally along the second side of the pad, and respective third portions extending generally along the top end of the pad. One of the lines of the first set of lines has a fourth portion extending generally along the bottom end of the pad. The second set of lines is located adjacent the bottom end of the pad and extend parallel to the longitudinal axis. The first set of lines merge with the second set of lines adjacent the bottom end of the pad.

The parallel lines form a barrier resistant to the egress of fluid out of the periphery of the pad and to channel fluid therealong to spread the fluid across the pad.

DETAILED DESCRIPTION OF THE PREFERRED EMBODIMENT

Figures 1, 2:
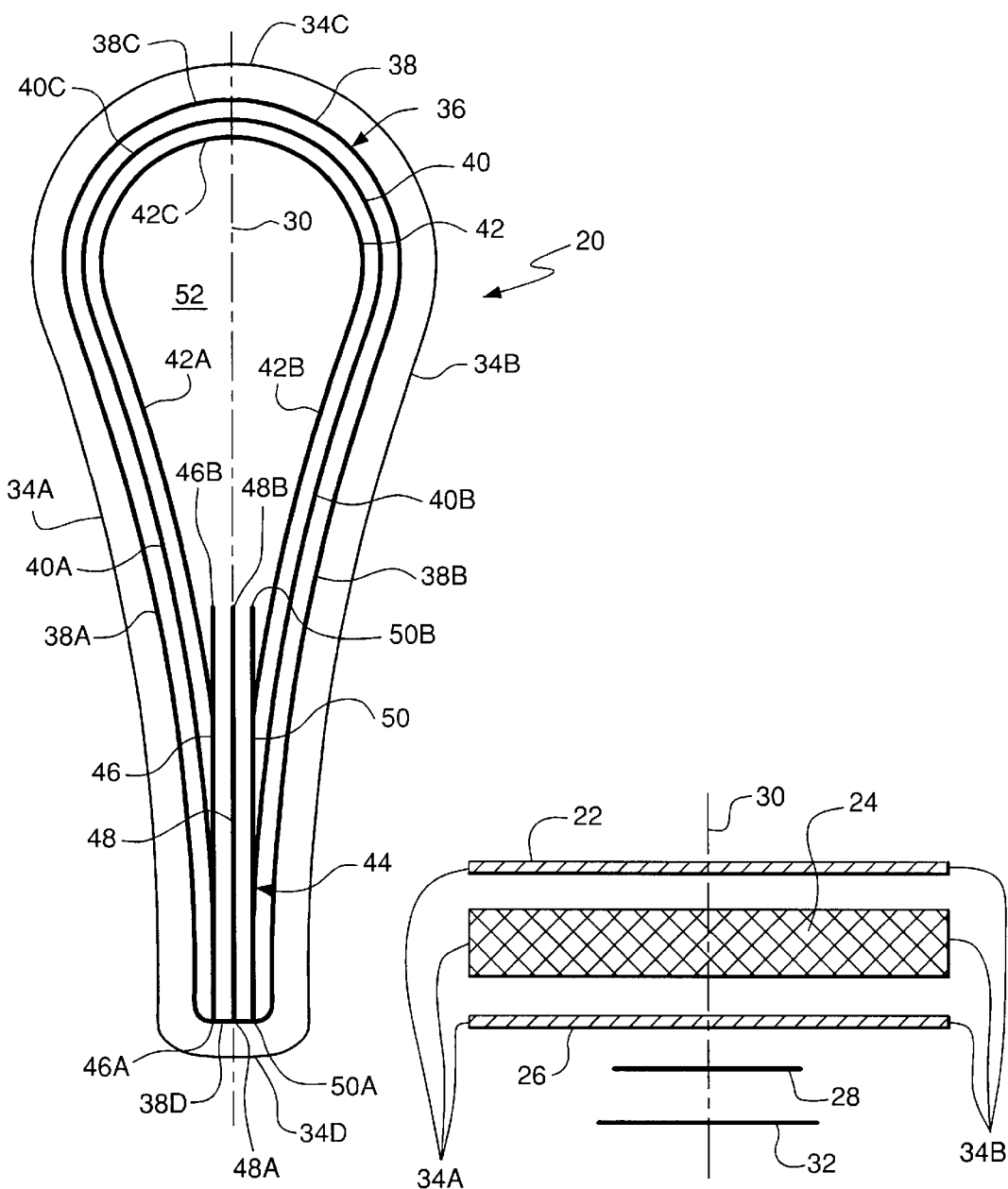
FIG. 1 is a plan view of one preferred exemplary embodiment of an absorbent thongshaped pantiliner constructed in accordance with this invention.
FIG. 2 is an enlarged, exploded, transverse cross sectional view of the pad shown in FIG. 1.

Referring now to the various figures of the drawing wherein like reference characters refer to like parts, there is shown in FIG. 1 a disposable pantiliner 20 which is shaped to be worn under a thong garment, e.g., thong underwear, and which is constructed in accordance with one embodiment of this invention. It should be pointed out that as used herein the term "disposable" means that article is designed to be used until soiled, either by urination or otherwise, and then discarded, rather than being washed and used again.

The pantiliner 20 basically comprises a thin generally planar structure or pad that may be any thickness in the range of 1 mm to 12 mm, with 3 mm being one preferred thickness. As can best be seen in FIG. 2, the pad is formed of a liquid pervious inner liner sheet 22, a liquid absorbent, e.g., air-laid composite, core 24, and an outer cover or back sheet 26 forming a moisture barrier. The inner liner may be of any liquid pervious material.

One particularly suitable material is a 15 gsm wettable nonwoven coverstock, made of spun bond polypropylene, available from BBA Nonwovens. The inner liner 22 is disposed directly on-top of the absorbent core 24 and, if desired may be secured thereon by a low add-on adhesive (not shown). One particularly suitable material for the adhesive is available from National Starch and Chemical of Bridgewater, N.J. under the trade designation 34-5637. The inner liner 22 may be formed of other material fibers (e.g., polyethylene, bi-component, polyester, rayon, cotton, etc.), fiber combinations (e.g., spunbond, air laid, wet laid, carded, hydroentangled, etc.), and basis weights may be used as well. In fact, if desired, the inner liner 22 may be formed of a liquid impermeable material, e.g., three dimensional polymeric film, having plural apertures or pores extending therethrough so as to make the material liquid permeable. One particularly suitable polymeric film is that disclosed in U.S. Design Letters Pat. No. 362,120, which patent is assigned to the same assignee as this invention and whose disclosure is incorporated by reference herein.

The back sheet or moisture barrier 26 is disposed directly over the other side of the absorbent core 24, i.e., on the opposite side from the inner liner 22, and, if desired may be secured thereon by a high add-on adhesive (not shown, like that which may be used to secure the inner liner 22 to the core 24).

The core 24 can be made up of any suitable absorbent material, as well as combinations of different types of absorbent material(s). For example, in one preferred embodiment shown herein the absorbent core 24 is formed of an air-laid absorbent material, such as wood pulp, and which optionally can contain a super absorbent polymer powder (SAP) and a binder. Examples of SAP include polyacrylamides, polyvinyl alcohol, polyacrylates, various grafted starches, and the like. One particularly suitable super absorbent material is a cross-linked polysodium acrylate, which can be purchased from Chemdal Corporation, Palatine, Ill. under the trade designation ASAP 2100.

If desired the pad 20 may include a fluid acquisition or transfer layer (not shown) located between the inner liner 22 and the core 24. As is known a fluid acquisition layer serves to manage, transport, accommodate and/or direct high volumes and flow rates of urine into the core. The fluid acquisition layer can be of any type construction, e.g., a thruto air bonded/carded web, a spunbond bicomponent non-woven web, a web of crosslink cellulosic fibers, apertured 3D (three dimensional) film or the like.

In order to hold the pad 20 in place within the wearer's thong undergarment, it includes a stripe 28 (FIG. 2) of a "positioning" adhesive on the outer surface of the moisture barrier 26 extending along the longitudinal central axis 30 of the pad for substantially the length of the pad. Any suitable positioning adhesive can be used for the stripe, such as a pressure sensitive hot melt adhesive. One particularly suitable material for the positioning adhesive 28 is available from National Starch and Chemical of Bridgewater, N.J. under the trade designation 34-5598. In order to protect the positioning adhesive stripe 28 from degradation or being soiled by debris, a single release strip 32 (e.g., a release paper) is releasably secured over the stripe as shown in FIG. 2. The release strip 32 can be formed of any suitable adhesive protective, yet easy to release, material. One particularly suitable material for the release strip 32 is available from DCP Lohja, Inc. of Willowbrook, IL under the trade designation ESP 39.

As best seen in FIG. 1 the periphery or outer profile of the pad 20 is of a general wedge shape, which is symmetrical with respect to the central longitudinal axis 30. In particular, the periphery of the pad 20 has a pair of tapering, e.g., convex arcuate, sides 34A and 34B, extending on either side of the axis 30, an arcuate, e.g., convex, top end 34C joining the upper ends of the sides 34A and 34B, and an arcuate, e.g., convex, lower end 34D joining the lower ends of the sides 34A and 34B. The inner layer 22, the core 24 and the back sheet 26 are each of the exact same size and shape and are disposed coincident with each other so that their respective marginal edges form the marginal edge or periphery of the pad 20.

In accordance with the exemplary embodiment shown in FIG. 1, the longitudinal dimension of the pad 20, i.e., the maximum distance between the arcuate ends 34C and 34D along the central longitudinal axis 30 is approximately 152 mm, whereas the lateral dimension measured transversely across the pad at its widest dimension, i.e., the points where the upper ends of the two sides 34A and 34B merge with the ends of the top end 34C, is approximately 60 mm. The radius of curvature of each of the sides 34A and 34B is 293.4 mm. The top end 34C has a radius of curvature of 30 mm and merges with the top ends of the two sides 34A and 34B. The bottom end 34D has a radius of curvature of 28 mm and merges with the bottom ends of the two sides 34A and 34B. It should be pointed out at this juncture that the foregoing dimensions and shapes of the pad 20 are merely exemplary and other dimensions and shapes can be utilized in accordance with this invention, so long as the pad is of a general wedge-shape conducive to be worn under a thong-shaped garment or undergarment.

In order to prevent the migration of liquid, e.g., urine or menses, laterally out of the pad 20, as well as to ensure that such liquid is directed throughout the pad into its core 24 for trapping therein, the pad 20 includes a plurality of parallel barrier lines (to be described later). Each of the barrier lines is arranged to form a somewhat dense wall across which fluid is deterred from flowing, while helping to direct or "channel" the fluid to flow therealong.

Each barrier line is produced by applying pressure and/or heat to the portions of the pad along the line to compress and increase the density of the materials along those lines, e.g., to compress the core 24. Depending upon the construction of the pad, the compression and/or heat applied to the materials making up the pad (particularly its core) causes the interstitial space between the individual fibers making up the core (any other layers of the pad composed of fibrous material) to compress or become densified to the point at which such densified areas are insufficient to allow liquid to flow therethrough. The application of pressure and heat can be accomplished using conventional thermal or ultrasonic bonding techniques or by pattern embossing. In some applications the use of pressure alone may be sufficient to produce a dense barrier line which remains after the pressure is removed. Moreover, an adhesive may be used when pressure is applied to create the dense barrier line. In fact, it is contemplated that water can be used in lieu of an adhesive for use with a core of suitable material so that after the pressure is released and the core dries the previously wet and compressed portions of the core will remain compressed, thereby forming the barrier lines.

In the embodiment 20 shown in FIG. 1 there are two sets of three parallel barrier lines in each set. In particular, the first set of barrier lines, designated by the reference number 36, is made up of three parallel, non-linear, barrier lines 38, 40, and 42. The barrier line 38 is the outermost of the barrier lines of the first set 36 and comprises three portions, namely, a first portion 38A extending along and generally parallel to the side 34A, a second portion 38B extending along and generally parallel to the side 34B, a third portion 38C extending along and generally parallel to the top end 34C and a fourth portion 38D extending along and generally parallel to the bottom end 34D. Thus, the outer barrier line 38 completely encircles the periphery of the pad 20 and is located approximately 5 mm from the pad's periphery all along the periphery. The barrier line 42 is the innermost of the barrier lines of the first set 36 and is of the same shape as the outermost barrier line 38 and is disposed parallel thereto. The innermost barrier line 42 comprises three portions, namely, a first portion 42A extending along and generally parallel to the side 34A, a second portion 42B extending along and generally parallel to the side 34B, and a third portion 42C extending along and generally parallel to the top end 34C. The barrier line 40 is the intermediate of the barrier lines of the first set 36. It is of the same shape as outermost and innermost barrier lines 38 and 42, respectively, and is located equidistantly therebetween, e.g., spaced from each by 2 mm. The intermediate barrier line 40 comprises three portions, namely, a first portion 40A extending along and generally parallel to the side 34A, a second portion 40B extending along and generally parallel to the side 34B, and a third portion 40C extending along and generally parallel to the top end 34C.

The second set of barrier lines, designated by the reference number 44, is made up of three parallel, linear, barrier lines 46, 48, and 50. The barrier line 48 is the central barrier line and extends along the central longitudinal axis 30 from its lower end 48A to its upper end 48B, a position slightly below the midpoint along the length of the pad. The lower end 48A of the barrier line 48 merges with the portion 38D of the outermost barrier line 38 of the first set 36. The barrier lines 46 and 50 of the second set 44 are located on opposite sides of the barrier line 48 equidistantly spaced therefrom. The lower end 46A of the barrier line 46 merges with the portion 38D of the outermost barrier line 38 adjacent the side 34A. The upper end 46B of the barrier line 46 terminates at the same height as the barrier line 48. The lower end 50A of the barrier line 50 merges with the portion 38D of the outermost barrier line 38 adjacent the side 34B. The upper end 50B of the barrier line 50 terminates at the same height as the barrier line 48.

The lower ends of the side portions 42A and 42B of the innermost barrier line 42 of the first set 36 merge with the barrier lines 46 and 50, respectively, just below the top ends of the lines 46 and 50. The lower ends of the side portions 40A and 40B of the intermediate barrier line 42 of the first set 36 merge with the barrier lines 46 and 50, respectively, approximately half way down the length of the lines 46 and 50.

The area 52 of the pad within the boundary defined by the innermost barrier line 42 and the top ends of the barrier lines 46,48 and 50 forms the "target area" for the fluid, e.g., urine and/or menses, insult, e.g., the point at which urine and/or menses first engages the pad. Irrespective of the point at which the fluid insult occurs within the target area 52 the material making up the pad's core 24 will cause the fluid to spread out across the target area. The innermost barrier line 42 will tend to prevent migration of the fluid across it and instead will tend to direct the fluid along it. Since the lower end of the pad will be disposed lower on the wearer's anatomy than the upper portion when the pad is in place, the urine and/or menses fluid will tend to migrate downward due to the influence of gravity. This downward migration may carry the fluid to the open spaces between the upper ends of the barrier lines 46, 48 and 50 where it can migrate downward unimpeded into the portions of the pad between those barrier lines. Migration of fluid out of the bottom end 34D of the pad 20 will be deterred by the barrier line portion 38D. If the fluid insult is sufficiently great some of the fluid will tend to migrate through the innermost barrier line 42 into the area between it and the intermediate barrier line 40, whereupon the intermediate barrier line will tend to prevent migration thereacross, and will direct the fluid along it and downward under the influence of gravity. Fluid which may migrate across the intermediate barrier line 40 will tend to be prevented from migrating out the periphery of the pad 20 by the outermost barrier line 38. That line will also serve to direct any fluid gaining ingress to the space between it and the intermediate barrier line 40 therealong and downward under the influence of gravity. Thus, the barrier lines of the two sets 36 and 44 will cooperate with each other to prevent or limit fluid migration or transfer out of the perimeter or edge of the pad, while spreading the fluid out across a substantial area of the pad to enable the pad to have a relatively high fluid capacity. As an extra measure of insurance against fluid egress from the periphery of the pad, a relative large space, e.g., approximately 5 mm, is provided between the periphery of the pad 20 and the outermost barrier line 38.

Figure 3:
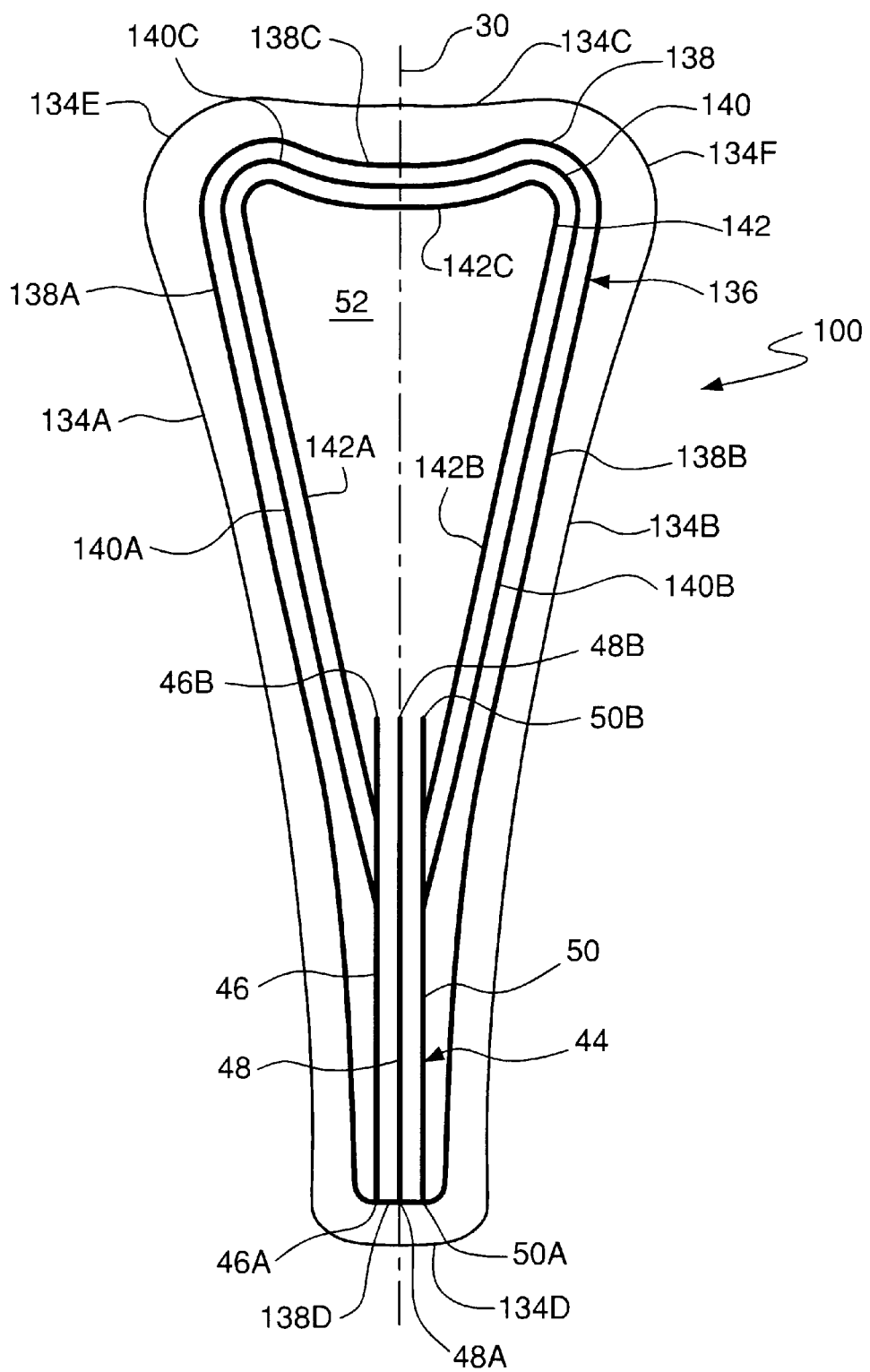
FIG. 3 is a plan view, similar to FIG. 1, but showing another preferred embodiment of an exemplary thong-shaped pantiliner constructed in accordance with this invention.

In FIG. 3 there is shown an alternative embodiment of a thong-shaped pantiliner pad 100 constructed in accordance with this invention. The pad 100 is identical in construction to the pad 20 described heretofore except for the shape of some of the portions of the pad and the shape of some of its barrier lines. In the interest of brevity the common components of the pads 20 and 100 will be given the same reference numbers and the details of their construction and operation will not be reiterated. Thus, as can be seen the periphery or outer profile of the pad 20 is of a general wedge shape which is symmetrical with respect to the central longitudinal axis 30. In particular, the periphery of the pad 100 has a pair of tapering, e.g., convex arcuate, sides 134A and 134B, extending on either side of the axis 30, an arcuate, e.g., concave, top end 134C joining the upper ends of the sides 134A and 134B, and an arcuate, e.g., convex, lower end 34D joining the lower ends of the sides 134A and 134B. The inner layer 22, the core 24 and the back sheet 26 are each of the exact same size and shape are disposed coincident with each other so that their respective marginal edges form the marginal edge or periphery of the pad.

In accordance with the exemplary embodiment shown in FIG. 3, the longitudinal dimension of the pad 100, i.e., the maximum distance between the ends 134C and 134D along the central longitudinal axis 30 is approximately 145 mm, whereas the lateral dimension measured transversely across the pad at its widest dimension, i.e., the points where the upper ends of the two sides 134A and 134B merge with the ends of the top end 134C, is approximately 64 mm. The radius of curvature of each of the sides 134A and 134B is 393.7 mm. The central or convex portion of the top end 134C has a radius of curvature of 75 mm and merges with the top ends of the two sides 134A and 134B at respective rounded corners 134E and 134F, respectively. The radius of curvature of the rounded corners 134E and 134F is 14.3 mm. The bottom end 34D of the pad 100 has a radius of curvature of 28 mm and merges with the bottom ends of the two sides 134A and 134B.

It should be pointed out at this juncture that the foregoing dimensions and shapes of the pad 100, like that of pad 20, are merely exemplary and other dimensions and shapes can be utilized in accordance with this invention, so long as the pad is of a general wedge-shape conducive to be worn under a thong-shaped garment or undergarment.

The pad 100 includes a plurality of parallel barrier lines formed in the same manner as described with reference to pad 20. Like pad 20, pad 100 includes two sets of three parallel barrier lines in each set. In particular, the first set of barrier lines, designated by the reference number 136, is made up of three parallel, non-linear, barrier lines 138,140, and 142. The barrier line 138 is the outermost of the barrier lines of the first set 136 and comprises three portions, namely, a first portion 138A extending along and generally parallel to the side 134A, a second portion 138B extending along and generally parallel to the side 134B, a third portion 138C extending along and generally parallel to the top end 134C and a fourth portion 38D extending along and generally parallel to the bottom end 34D. The portion 138A is partially linear and partially arcuate (concave). Portion 138B is also partially linear and partially arcuate (concave). The portion 138C is partially concave (in its center) and convex at its rounded ends. The outer barrier line 138, like barrier line 38 of the pad 20, completely encircles the periphery of the pad 100 and is located the same distance from the pad's periphery as the barrier line 38 of the pad 20. The barrier line 142 is the innermost of the barrier lines of the first set 136 and is of the same shape as the outermost barrier line 38 and is disposed parallel thereto. The innermost barrier line 142 comprises three portions, namely, a first portion 142A extending along and generally parallel to the side 134A, a second portion 142B extending along and generally parallel to the side 134B, and a third portion 142C extending along and generally parallel to the top end 134C. The barrier line 140 is the intermediate of the barrier lines of the first set 136. It is of the same shape as outermost and innermost barrier lines 138 and 142, respectively, and is located equidistantly therebetween. The intermediate barrier line 140 comprises three portions, namely, a first portion 140A extending along and generally parallel to the side 134A, a second portion 140B extending along and generally parallel to the side 134B, and a third portion 140C extending along and generally parallel to the top end 134C. The spacing between the barrier lines 138, 140 and 142 of the pad 100 is the same as the spacing between the barrier lines 38, 40 and 42 of the pad 20.

The second set of barrier lines, designated by the reference number 44, is made up of three parallel, linear, barrier lines 46, 48, and 50. The barrier line 48 is the central barrier line and extends along the central longitudinal axis 30 from its lower end 48A to its upper end 48B, a position slightly below the midpoint along the length of the pad. The lower end 48A of the barrier line 48 merges with the portion 38D of the outermost barrier line 138 of the first set 136. The barrier lines 46 and 50 of the second set 44 are located on opposite sides of the barrier line 48 equidistantly spaced therefrom. The lower end 46A of the barrier line 46 merges with the portion 138D of the outermost barrier line 138 adjacent the side 134A. The upper end 46B of the barrier line 46 terminates at the same height as the barrier line 48. The lower end 50A of the barrier line 50 merges with the portion 38D of the outermost barrier line 138 adjacent the side 134B. The upper end 50B of the barrier line 50 terminates at the same height as the barrier line 48.

The lower ends of the side portions 142A and 142B of the innermost barrier line 142 of the first set 136 merge with the barrier lines 46 and 50, respectively, just below the top ends of the lines 46 and 50. The lower ends of the side portions 140A and 140B of the intermediate barrier line 142 of the first set 136 merge with the barrier lines 46 and 50, respectively, approximately 40% down the length of the lines 46 and 50.

The area 152 of the pad 100 within the boundary defined by the innermost barrier line 142 and the top ends of the barrier lines 46, 48 and 50 forms the "target area" for the fluid insult. The pad 100 operates to spread the fluid insult thereacross while preventing migration of the fluid out of the periphery of the pad in the same manner as discussed above with respect to pad 20, so that such operation will not be reiterated.

It should be pointed out at this juncture that pads constructed in accordance with this invention can be of various shapes and/or sizes and/or constructions. Moreover, the pads can include any plural number of barrier lines, with the shape of those lines being either the same as that of the pad or of different shapes.

Without further elaboration the foregoing will so fully illustrate my invention that others may, by applying current or future knowledge, adopt the same for use under various conditions of service.

I claim:

1. A disposable pantiliner for a thong garment, said pantiliner being arranged to be worn by a wearer to trap and collect fluid waste products of the wearer, said pantiliner being an elongated generally planar pad having a longitudinal central axis and a generally wedge-shaped periphery including first and second generally longitudinal extending sides interconnecting a top end and a bottom end, said top end having a substantially longer periphery than said bottom end, said pad comprising a top-sheet, a fluid absorbent core, and a back sheet, said top sheet being formed of a fluid pervious material and being disposed over said absorbent core, said absorbent core comprising a fluid absorbing material and being disposed over said back sheet, said back sheet being formed of a fluid impervious material, said top-sheet, said fluid absorbent core and said back sheet being bonded together along first and second sets of plural generally parallel lines, said first set of generally parallel lines having respective first portions extending generally along said first longitudinally extending side of said pad, respective second portions extending generally along said second longitudinally extending side of said pad, and respective third portions extending generally along said top end of said pad, one of said lines of said first set of generally parallel lines having a fourth portion extending generally along said bottom end of said pad, said second set of generally parallel lines being located adjacent said bottom end of said pad and extending parallel to said longitudinal central axis, said first set of generally parallel lines merging with said second set of generally parallel lines adjacent said bottom end of said pad, said first set and second set of generally parallel lines cooperating to form a barrier resistant to the egress of fluid out of the periphery of said pad and to channel fluid therealong to spread the fluid across said pad.

2. The pantiliner of claim 1 wherein said first set of generally parallel lines comprises three lines, an outer one of said first set of generally parallel lines being located closest to the periphery of said pad, an inner one of said first set of generally parallel lines being located closest to the central longitudinal axis of said pad, and an intermediate one of said first set of generally parallel lines being located between said inner and outer ones of said first set of generally parallel lines.

3. The pantiliner of claim 1 wherein said fluid absorbent core comprises cellulosic fibers.

4. The pantiliner of claim 1 additionally comprising a cover sheet.

5. The pantiliner of claim 1 wherein said top end is somewhat convex.

6. The pantiliner of claim 5 wherein said bottom end is somewhat convex.

7. The pantiliner of claim 6 wherein said first set of generally parallel lines is non-linear and said second set of lines is linear.

8. The pantiliner of claim 1 wherein said top sheet is selected from the group consisting of spun bonded or carded web non-woven materials or apertured three dimensional plastic film.

9. The pantiliner of claim 8 wherein said fluid absorbent core additionally comprises absorption enhancing materials.

10. The pantiliner of claim 9 wherein said cover sheet is formed of a plastic material selected from the group consisting of polypropylene, polyester, polyethylene, and blends thereof.

11. The pantiliner of claim 1 wherein said top end is somewhat concave.

12. The pantiliner of claim 11 wherein said bottom end is somewhat convex.

13. The pantiliner of claim 12 wherein said first set of generally parallel lines is non-linear and said second set of generally parallel lines is linear.

14. The pantiliner of claim 13 wherein said third portions of said first set of generally parallel lines are generally parallel to the top end of said pad.

15. The pantiliner of claim 1 wherein said first and second portions of said first set of parallel lines are parallel to said first longitudinally extending side and said second longitudinally extending side, respectively, of said pad.

16. The pantiliner of claim 15 wherein said fourth portion of said first set of generally parallel lines is generally parallel to the bottom end of said pad.

17. The pantiliner of claim 16 wherein said one of said generally parallel lines of said first set having said fourth portion being said outer one of said first set of generally parallel lines.

18. The pantiliner of claim 17 wherein said inner one of said first set of generally parallel lines includes a pair of lower ends, one of said lower ends of said inner one of said first set of generally parallel lines merging with one of said outer ones of said second set of generally parallel lines and the other of said lower ends of said inner one of said first set of generally parallel lines merging with the other of said outer ones of said second set of generally parallel lines.

19. The pantiliner of claim 16 wherein said second set of generally parallel lines comprises three lines, a first outer one, a second outer one and an inner one, said inner one of said second set of lines extending along said central longitudinal axis, one of said outer ones of said second set of generally parallel lines being located between said inner one of said second set of generally parallel lines and the periphery of said pad, the other of said outer ones of said second set of generally parallel lines being located between said inner one of said second set of generally parallel lines and the periphery of said pad.

20. The pantiliner of claim 19 wherein each line of said second set of generally parallel lines includes a lower end that merges with said fourth portion of said outer one of said first set of lines.

21. The pantiliner of claim 20 wherein said intermediate one of said first set of generally parallel lines includes a pair of lower ends, one of said lower ends of said intermediate one of said first set of generally parallel lines merging with one of said outer ones of said second set of generally parallel lines and the other of said lower ends of said intermediate one of said first set of generally parallel lines merging with the other of said outer ones of said second set of generally parallel lines .

* * * * *